US00PP12130P2

(12) United States Plant Patent
Zary

(10) Patent No.: US PP12,130 P2
(45) Date of Patent: Oct. 9, 2001

(54) FLORIBUNDA ROSE PLANT NAMED 'JACREX'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/405,427

(22) Filed: Sep. 22, 1999

(51) Int. Cl.[7] ..... A01H 5/00
(52) U.S. Cl. ..... Plt./144
(58) Field of Search ..... Plt./144, 145, 133, Plt./134, 103, 104

*Primary Examiner*—Howard J. Locker
(74) *Attorney, Agent, or Firm*—Klarquist Sparkman Campbell Leigh & Whinston, LLP

(57) ABSTRACT

A floribunda rose plant having a vigorous, upright plant habit; good disease resistance; ability to grow well in its own roots; glossy foliage; and large, open clusters of many petaled white flowers.

1 Drawing Sheet

1

The present invention relates to a new and distinct variety of rose plant of the floribunda class which was originated by me by crossing the variety 'Iceberg' (not patented), with the variety 'MACrexy' (U.S. Plant Pat. No. 6,713).

The primary objective of this breeding was to produce a new rose variety having the vigorous, upright plant habit, good disease resistance and ability to grow well on its own roots of the female parent, combined with the profuse flowering, many petaled flowers and glossy foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Large, open clusters;
2. Constant blooming;
3. Large, vigorous, upright, well-branched plant;
4. Good disease resistance; and
5. Ability to grow well on its own roots.

Asexual reproduction of this new variety by softwood cuttings, as performed at Wasco, Calif., shows that the foregoing and all other characteristics and distinctions come true to form and are established and transmitter through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—'Iceberg' (not patented).

*Pollen parent.*—'MACrexy' (U.S. Plant Pat. No. 6,713).

Classification:

*Botanical.*—*Rosa hybrida.*

*Commercial.*—Floribunda.

2

FLOWER

Observations made from specimens grown in a garden environment at Somis, Calif. from March 1998 to August 1999.

Blooming habit: Continuous.

Bud:

*Size.*—1¼ inches long when the petals start to unfurl.

*Form.*—The bud form is long; pointed ovoid.

*Color.*—When sepals first divide, bud color is Yellow-White Group 158D. When half brown, the upper and lower sides of the petals are Yellow-White Group 158D.

*Sepals.*—Color: Green Group 138B. Surface texture: Covered in fine hairs. There are three lightly appendaged sepals. There are two unappendaged sepals with hairy edges.

*Receptacle.*—Color: Green Group 137A. Shape: Funnel. Size: Medium (about ⅜ inch ×¼ inch). Surface: Smooth.

*Peduncle.*—Length: Short (about 1 to 1¼ inches). Surface: Glandular. Color: Green Group 137A. Strength: Stiff; erect.

Bloom:

*Size.*—Medium. Average open size is 3 to 3½ inches.

*Borne.*—Several together in flat clusters of five to nine blooms.

*Stems.*—Strength: Strong. Average length is about 14—18 inches.

*Form.*—When first open, bloom is high centered. Permanence: Flattens.

*Petalage.*—Number of petals under normal conditions: 40–50.

*Color.*—The upper and reverse sides of the petals are Yellow-White Group 158D. The base of each petal has on the upper surface a ⅛ inch × ⅛ inch, Yellow Group 6D half moon at the point of attachment. The lower surface has a 1/16 inch ×1/16, inch Yellow Group 4C half moon at the point of attachment. The major color on the upper side is Yellow-White Group 158D.

*Variegations.*—None.

*Discoloration.*—The general tonality at the end of the first day: No change. At the end of the third day: No change.

*Fragrance.*—Slight.

Petal:

*Texture.*—Thick.

*Shape.*—Round to deltoid.

*Form.*—Tips slightly recurved.

*Arrangement.*—Imbricated. Petaloids in the center are few and irregular in shape ranging from ¼–½ inch long and ⅛–¼ inch wide. They number from 0 to 4 in a 10-flower sample. They are all Yellow-White Group 158D in color.

*Persistance.*—Petals drop off cleanly before drying.

*Lastingness.*—On the plant: Fair (about five to six days). As a cut flower: Fair (about six days).

Reproductive parts:

*Anthers.*—Size: Medium. Quantity: Many. Color: Yellow-Orange Group 16C. Arrangement: Regular around styles.

*Filaments.*—Color: Yellow Group 9C.

*Pollen.*—Present.

*Styles.*—Color: Red Group 53C.

*Stigmas.*—Color: Orange-White Group 159B.

Plant:

*Form.*—Bush.

*Growth.*—Vigorous; upright; branching. At maturity, height is 48 inches, width is 36 inches.

Foliage: Number of leaflets on normal mid-stem leaves: Five or seven.

*Size.*—Medium (5 inches long×3½ inches wide).

*Quantity.*—Abundant.

*Color.*—New foliage: Upper and lower surfaces: Greyed-Red Group 178A. Old foliage: Upper surface: Green Group 139A. Lower surface: Green Group 139B.

Leaflets:

*Shape.*—Pointed oval.

*Texture.*—Leathery; glossy.

*Edge.*—Serrated.

*Serration.*—Single; small.

*Petiole rachis.*—Color: Upper: Green Group 139A. Lower: Green Group 139B.

*Petiole underside.*—Rough, with prickles.

*Stipules.*—Medium (about ⅝ inch); serrated; bearded.

*Disease resistance.*—Resistant to mildew and rust; susceptible to blackspot under normal growing conditions.

Wood:

*New wood.*—Color: Greyed-Red Group 178B. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 183A.

*Color when mature.*—Greyed-Orange Group 165A.

Small prickles:

*Quantity.*—On main stalks: None. On laterals: None.

I claim:

1. A new and distinct variety of rose plant of the floribunda class, substantially as herein shown and described, characterized particularly by its vigorous, upright plant habit; good disease resistance; ability to grow well on its own roots; glossy foliage; and large, open clusters of many petaled white flowers.

* * * * *

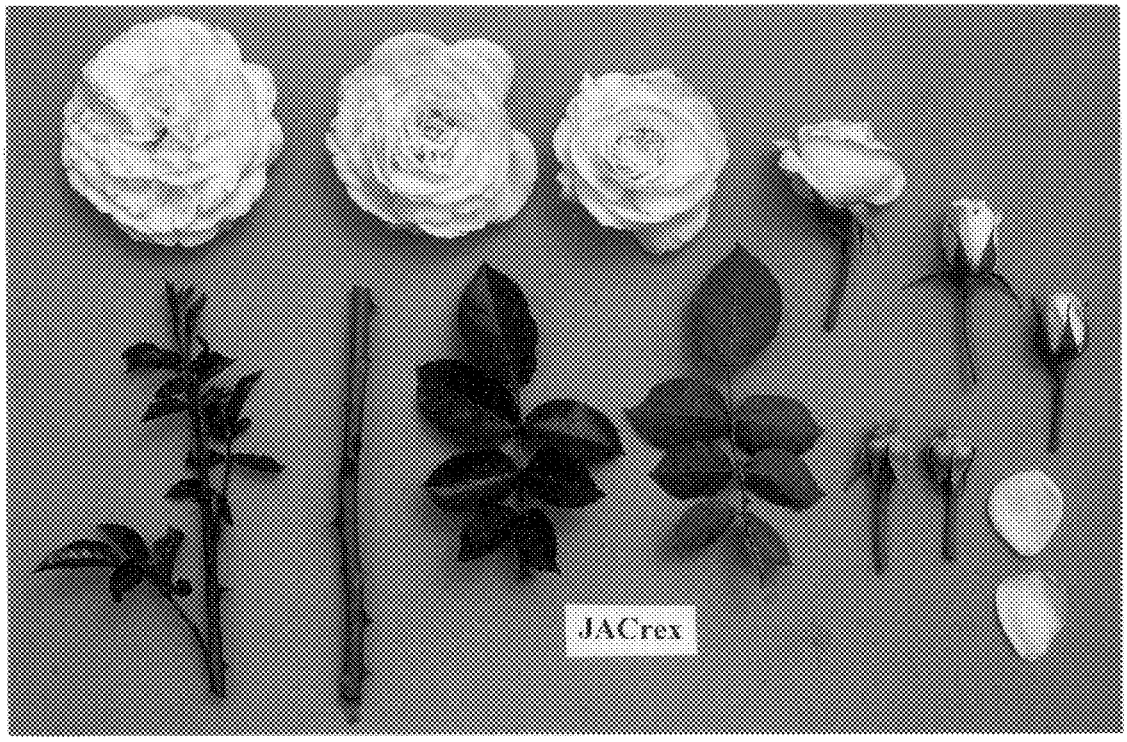
JACrex